United States Patent [19]
Gudin

[11] 3,955,317
[45] May 11, 1976

[54] METHOD OF GROWING PLANT CELLS

[75] Inventor: Claude Gudin, Palette, France

[73] Assignee: The British Petroleum Company Limited, London, England

[22] Filed: Jan. 27, 1975

[21] Appl. No.: 544,361

[30] Foreign Application Priority Data
Jan. 28, 1974 United Kingdom............... 3806/74

[52] U.S. Cl.................................. 47/1.2; 47/1.4; 47/58
[51] Int. Cl.² ........................................ A01G 31/00
[58] Field of Search ................. 47/58, 1.4, 1.2, 17

[56] References Cited
UNITED STATES PATENTS

| 2,715,795 | 8/1955 | Pallotta et al......................... 47/1.4 |
| 2,732,663 | 1/1956 | Dewey .................................. 47/1.4 |
| 2,807,912 | 10/1957 | Bjorksten............................... 47/58 |
| 3,385,786 | 5/1968 | Klock.................................... 47/1.4 |
| 3,402,506 | 9/1968 | Renfro.................................. 47/1.2 |
| 3,468,057 | 9/1969 | Buisson et al......................... 47/1.4 |
| 3,579,907 | 5/1971 | Graves.................................. 47/17 |

Primary Examiner—Robert E. Bagwill
Attorney, Agent, or Firm—Morgan, Finnegan, Pine, Foley & Lee

[57] ABSTRACT

Plant cells are grown continuously in a tubular transparent plastic structure through which water containing nutrients and carbon dioxide are passed. A suspension of plant cells in the water grow on exposure to light and can be harvested as a food material.

6 Claims, 3 Drawing Figures

METHOD OF GROWING PLANT CELLS

This invention relates to a method for growing plant cells or unicellular algae in liquid suspension.

The growth of plant cells containing chloroplaste in liquid shake cultures or an agar media is a technique which has been used for the growth of various types of plants. A technique is described in the American Journal of Botany, 1963, Vol. 50 pages 248–254, in an article by A. C. Hildebrandt, J. C. Wilmar, H. Johns and A. J. Riker.

Basically the technique involves taking an aseptic callus from part of a plant, tranferring it to a growth medium and exposing the tissue to light. The tissue will grow in the growth medium. Similar techniques can also be used to grow plant cells in suspension in a liquid nutrient medium.

There are many well known nutrient media which have been used for plant cell culture. They usually contain various minerals needed as nutrients, sometimes called macro-elements, and various metal salts, sometimes called micro-elements. Various amino acids, vitamins and plant growth regulators can also be present. Examples of common nutrient media are Skoog, Heller, Knop, Skoog and Murashige, Gamborg, White and Street media. These media contain various amounts of the various ingredients. As a source of carbohydrate sucrose, glucose and coconut milk have been used.

Typical macro-elements include compounds of nitrogen, phosphorus, potassium, calcium and magnesium, typical micro-elements include salts of iron, zinc, manganese, copper, nickel, molybdenum and boron.

The media used also contain growth regulators such as auxins and cytokinins, and amino acids and vitamins such as nicotinic acid thiamine, glycine and folic acid.

When plant cells are grown in glass shake vessels it has been found difficult to grow them on a large scale.

We have now devised an improved method for growing plant cells in a liquid suspension.

According to the invention there is provided a method for growing plant cells containing chloroplasts in liquid suspension in a growth medium in which method the liquid suspension is enclosed in an elongated, at least partially transparent container, and the container containing the suspension is supported by a body of water, the liquid suspension being exposed to light and brought into contact with carbon dioxide.

The transparent material can be any material, preferably flexible, which is not harmful to the plant tissue, is substantially water insoluble and water impermeable, and is transparent to visible light and the near ultra-violet.

Suitable materials include material made from polyolefins e.g. polyethylene and polypropylene, polyacrylates, polyamides, polycarbonates, water insoluble cellulose esters and polyester films. A preferred material is low density polyethylene.

Carbon dioxide is preferably brought into contact with the liquid suspension by bubbling a carbon dioxide containing gas through the suspension. Preferably air having an increased carbon dioxide content e.g. of up to 3.0% by volume, preferably of about 0.3% by volume is used.

The container can be supported by any expanse of water, for example lakes, reservoirs or seas by floatation. As the suspension is preferably subjected to mild agitation the sea is a preferred body of water on which to support the container.

The elongated container is preferably tubular with an inlet and an outlet, and water containing nutrients is passed in at the inlet and out at the outlet. The carbon dioxide gas can be passed through the water in the container either in the same direction as the flow of water through the container, or in the opposite direction.

In one embodiment of the invention a raft is formed of at least two tubes in which the tubes are connected zig-zag fashion so there is a continuous flow path through the raft.

The tubes can be joined together and held in a rigid frame so as to form a rigid raft. When a rigid raft is formed there can be walk ways around the edge of the raft to provide access to the tubes.

The tubes when full of liquid preferably have a depth of from 10 to 80 cm, e.g. about 30 cm, the depth of the tubes being such that adequate light can pass through the suspension of plant cells in the tube to allow a satisfactory growth rate throughout the tube.

The growth medium can be any of the well known nutrient media referred to above, the medium used being dependent on the cells being grown.

Preferably the cells of the plant grown are an autotrophic or photosynthetic strain so that no carbohydrate need be present. The absence of carbohydrate reduces the risk of bacterial contamination.

The degree of buoyancy in the container can be controlled by the amount of gas e.g. air, in the container, if the container is too low in the water then more gas can be fed into the container, if the container is too high in the water then gas in the container is replaced by water.

When the container is exposed to sunlight the temperature in the container will rise (the greenhouse effect) and if it is too high then, by sinking the container deeper into the water, more cooling is achieved by the supporting water. If the temperature in the container is too low then by causing the container to rest higher out of the water less cooling is caused by the supporting water and the temperature in the container will rise.

The container can be entirely made of transparent material, or the lower portion (substantially that portion not exposed to the sunlight in normal use) can be opaque.

The control of buoyancy can be achieved automatically by a temperature sensing device controlling air being fed to the apparatus or by a light detecting device e.g. a photo-electric cell which measures the intensity of light falling on the container. If a light detecting device is used then the readings from the device can be used to control the rate of carbon dioxide addition, as the greater the light intensity the greater the carbon dioxide requirement and photosynthesis and multiplication rates of the plant cells in suspension.

Preferably there is attached to the elongated container a buoyancy flotation means, for example a buoyancy member which can be filled with air or water so that the buoyancy of the apparatus can be controlled by means of the amount of air or water in this member.

When the flexible elongated member is a tube, the buoyancy member is preferably a tube joined lengthwise to the elongated member. Conventional air and water ports can be used to allow for ingress and egress of air and water.

When a raft of tubes held in a rigid frame is formed the buoyancy is preferably controlled by having a buoyancy member attached to each edge of the raft, and the relative amounts of liquid and gas in the buoyancy member is used to control the buoyancy of the raft.

The liquid suspension of plant tissue can be continuously removed and the tissue separated out to provide a continuous method of growing plant biomass. By controlling the rate of removal of the liquid suspension and the rate of addition of fresh nutrient medium it is possible to maintain the density of plant cells in suspensio at a desired level.

During daylight hours the light falling on the cells causes the cells to photosynthesise and to grow and, by continually removing liquid medium containing suspended plant biomass and adding fresh medium, the concentration of cells can be maintained substantially constant. The removed liquid can have the biomass removed e.g. by centrifugation, filtration, or sedimentation.

The preferred cellular density in the suspension is from 1 to 100 grms per liter, e.g. about 10 grams per liter.

It is known that certain bacteria can photosynthesise under certain conditions. These bacteria normally utilise light of a wavelength longer than that utilised by plants e.g. they can utilise light in the red and infra-red regions of the spectrum. Light in the red and infra-red region of the spectrum can pass through media which are opaque or semi-opaque to light in the visible portion of the spectrum.

When the container enclosing a suspension of cells of plant is exposed to sunlight, light in the visible portion of the spectrum is absorbed and reflected by the suspension, whereas light in the infra-red portion of the spectrum tends to pass through the suspension.

In the method of the present invention there is preferably a simultaneous growth of photosynthetic bacteria in a second container, which second container encloses a suspension of photosynthetic bacteria, the second container being attached to the container containing cells of plant tissue so that light passing through the container containing cells of plant tissue passes into the second container. This simultaneous growth can bring about a larger production of biomass for the same area covered by the container.

When the container containing a suspension of plant cells is tubular it can be divided into two along its length to form two sub-containers one on top of the other, the lower of the subcontainers containing a suspension of photosynthetic bacteria, and the upper most sub-container containing a suspension of plant cells. Preferably the division between the two sub-containers is a flexible transparent material e.g. of the same type as that of which the containers can be made.

As the photosynthetic bacteria adsorb light of a longer wave length than plant cells, adequate light can reach the photosynthetic bacteria even though it would not be adequate for plant cell growth.

The term plant cells includes photosynthetic unicellular algae e.g. of the genera Chlorella, Scenedesmus, Chlamydomonas and Spirulina both normal and cell wall deficient mutant strains.

In order to circulate the nutrient medium containing the plant cells a pump means is normally required, in an embodiment of the invention the preferred pump means is a heat pump. As the heat source for the heat pump a series of tubes smaller than the tubes through which the suspension of plant cells is circulating disposed adjacent to at least some of the length of those tubes can be used. These smaller tubes can be made of a dark light absorbing material e.g. a black plastics material and liquid passing through them is heated by action of the sun's rays, this heated liquid can then be used as the heat source for the heat pump.

For the growth of plant cells the more favoured wave lengths of light appear to be 440 nm and 660 nm. Light at the ultra-violet end of the spectrum is not normally utilised by plant cells. The incorporation in the material from which the container is made of known wave length shifters such as 1,4-di-[2-(5-phenyloxazoly]-benzene which can absorb radiation in the near ultra-violet and fluoresce at about 430 nm can be beneficial in increasing the amount of utilisable light falling on the plant cells.

The invention is further illustrated in the accompanying drawings in which.

Figure 1:
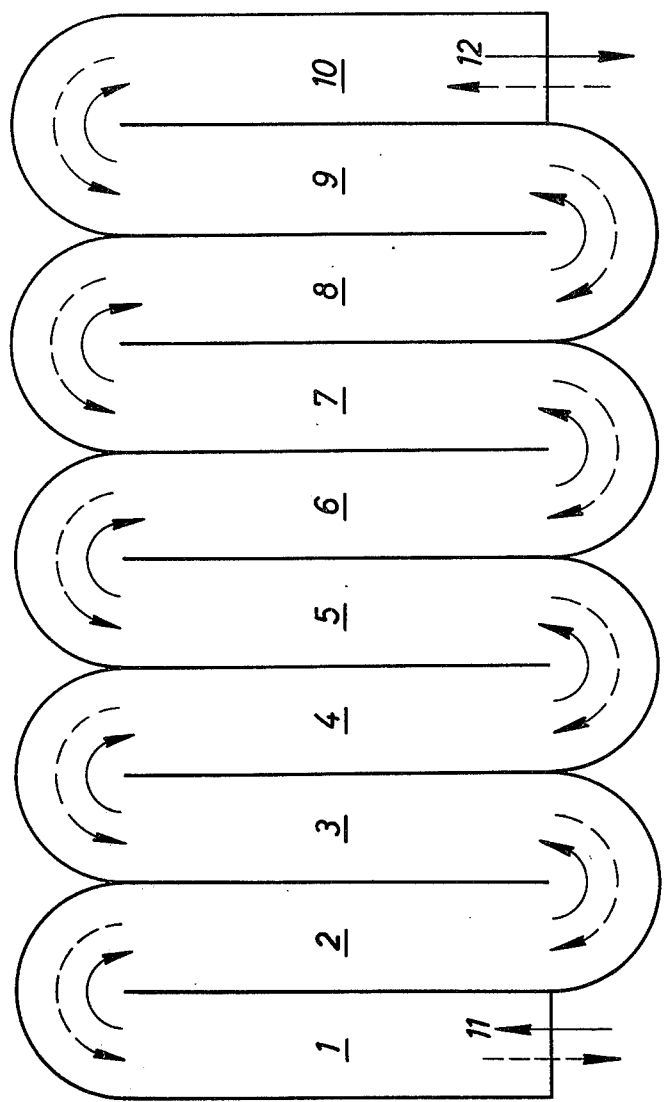
FIG. 1 is a plan view of an embodiment of the invention.

Referring to FIG. 1, a series of tubes 1 to 10 made of transparent material are connected together to form a raft. The tubes are connected as shown to provide a continuous path from one end of the raft to the other.

There is an inlet for liquid nutrient medium and outlet for gas at 11, and an outlet for liquid nutrient medium and inlet for gas at 12.

Figure 2:
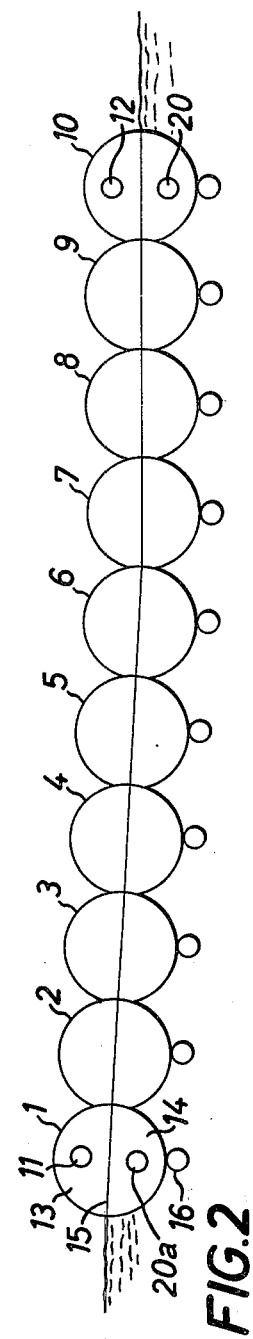
FIG. 2 is a side view of the embodiment shown in plan view in FIG. 1.

Referring to FIG. 2, each tube comprises an upper subcontainer 13, and lower sub-container 14, divided by a water and air impermeable membrane 15. Attached to the tubes is a smaller buoyancy tube 16. The inlets and outlets 11 and 12 lead to sub-container 13 only and there is a gas inlet and liquid outlet at 20, and gas outlet and liquid inlet for gas at 20a in sub-container 14.

In operation the raft is floated on an expanse of water and sub-container 13 is partly filled with an aqueous suspension of plant tissue, air containing increased carbon dioxide is passed in through inlet 12, and its flow through the raft to gas outlet 11 is shown by the broken arrows. Nutrient medium containing the nutrients required for growth of the plant cells is fed in through inlet 11 and its flow through the raft to liquid outlet 12 is shown by the solid arrows.

Sub-container 14 is filled with photosynthetic bacteria and nutrient medium for the bacteria is fed in through inlet 20a, and out through outlet 20, carbon dioxide is fed in through inlet 20a and out through outlet 20 the flow of gas and liquid through the sub-container 14 being in the same directions as in sub-container 13.

The raft is floated on water, and as sunlight passes into the tubes the plant tissue grows in sub-container 13 and bacteria grow in sub-container 14. The gas and nutrient medium flows are adjusted for each sub-container for the requisite growth.

The liquid output from each container is fed to a separator and the plant cells and bacteria are separated from their respective liquid outputs.

There are temperature sensing devices attached to the liquid in each of the sub-containers, and these temperature sensing devices control the amount of water and air in buoyancy tube 16. If the temperature of the liquid in the raft is too high, then the content of buoyancy tube 16 is adjusted to contain more water and less air so the raft floats lower in the water and there is more cooling. If the temperature of the liquid in the raft is too low then the content of buoyancy tube 16 is adjusted to contain more air and less water and the raft floats higher in the water and there is less cooling.

As the plant cells can grow at a faster rate at higher temperatures, then the temperature sensing devices can also control the flow rate of nutrient medium and air through the raft.

Figure 3:
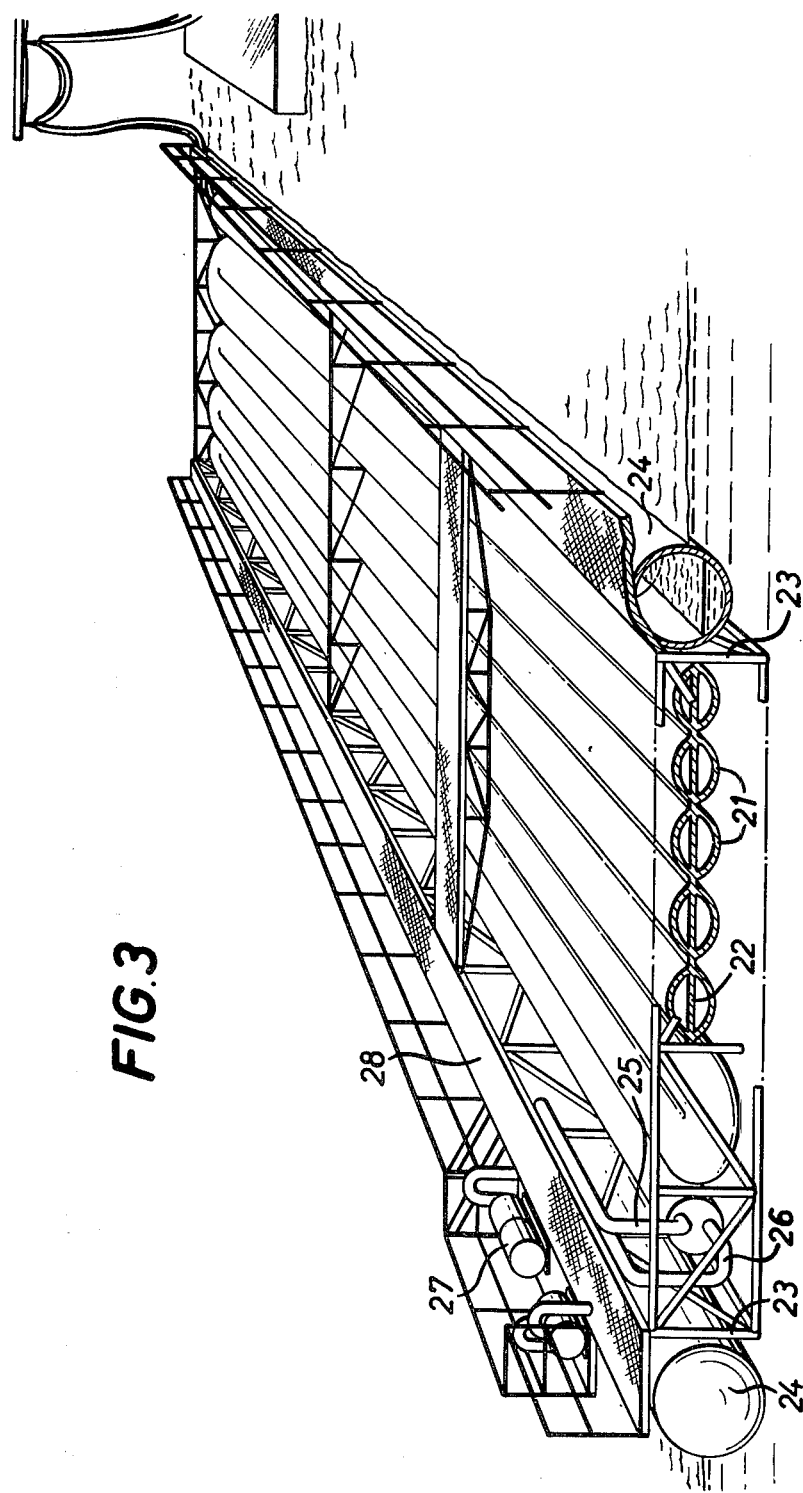
FIG. 3 is a schematic view of another embodiment of the invention with part cut away.

Referring to FIG. 3, a series of tubes 21 are divided into two by partitions 22, and are connected zig-zag fashion to form two continuous flow paths one above the other. The tubes are held in a rigid frame work 23 to form a raft. Connected to the frame work 23 are ballast tubes 24 which can have the amount of air and water in them varied. Pipes 25 and 26 are connected to pump 27 in order to pass liquid through the tubes 21, and there are liquid take off ports at end 27 of the tubes. There are walk-ways 28 over the ballast tubes 24 in order to provide ready access to the tubes.

In operation the raft is floated on an expanse of water and the upper part of the tubes above the partition 22 is filled with an aqueous suspension of plant tissue, air containing increased carbon dioxide content is passed in through pipe 25 and flows through the raft to take off point at the end 27. Nutrient medium containing the nutrients required for growth of the plant cells is passed counter current to the air. The lower part of the tubes 21 below the partition 22 is filled with photosynthetic bacteria, and nutrient medium and air containing carbon dioxide is passed through the lower part of the tube in the same directions as in the upper part of the tube.

The raft is floated on water and as sunlight passes into the tubes the plant tissue grows in the upper part of the tubes and the bacteria grow in the lower part of the tubes. The gas and nutrient medium flows are adjusted for each part of the tubes.

The liquid output from each part of the tubes is fed to a separator and the plant cells and bacteria are separated from their respective liquid outputs.

There are temperature sensing devices attached to the liquid in each of the sub-containers, and these temperature sensing devices control the amount of water and air in ballast tubes 24. If the temperature in the liquid in the raft is too high, then the content of the ballast tubes 24 is adjusted to contain more water and less air, so the raft floats lower in the water and there is more cooling. If the temperature of the water in the raft is too low then the contents of the ballast tubes 24 are adjusted to contain more air and less water and the raft floats higher in the water and there is more cooling.

I claim:

1. A method for growing plant cells containing chloroplasts in liquid suspension simultaneously with the growth of photosynthetic bacteria, in which method the liquid suspension containing the plant cells is enclosed in a first elongated, at least partially transparent, container and a liquid suspension of photosynthetic bacteria is contained in second elongated, at least partially transparent, container, the said second container being attached to the said first container so that light passing through the said first container then passes through the said second container; the said containers preventing passage of liquid from one container to the other, the containers being supported on a body of water; the liquid suspension in the first container being exposed to light and brought into contact with carbon dioxide.

2. A method as claimed in claim 1 in which the said liquid suspensions are passed continuously through the said first and second containers and plant cells and bacteria are separated from the respective suspensions containing them.

3. A method as claimed in claim 1 in which the temperature of the liquid suspensions is controlled by varying the cooling effect of the supporting water by varying the depth of immersion in the cooling water.

4. A method as claimed in claim 1 in which the said elongated chambers each comprise a plurality of tubes connected to form a raft, there being a continuous flow path through each of the said containers in the raft.

5. Apparatus for growing plant cells in liquid suspension which apparatus comprises a raft formed of at least two tubes made of at least partially transparent material connected in zig-zag fashion to form a continuous flow path through the raft, there being an inlet and an outlet for the tubes, and there being a buoyancy member attached to the raft whereby the buoyancy of the raft can be varied by altering the relative amounts of air and water in the buoyancy member; the tubes being divided into two separate compartments so that when the raft floats on water one compartment is above the other.

6. Apparatus as claimed in claim 5 in which the tubes when full of liquid have a depth of 10 to 80 cm.

* * * * *